(12) United States Patent
Khalaf

(10) Patent No.: US 6,292,628 B1
(45) Date of Patent: Sep. 18, 2001

(54) STEADY-TEMPERATURE WATER HEATER AND ENEMA DEVICE

(76) Inventor: Majid Z. Khalaf, 1817 S. Harlem Ave. Apt 8, Berwyn, IL (US) 60402

( * ) Notice: Subject to any disclaimer, the term of this patent is extended or adjusted under 35 U.S.C. 154(b) by 0 days.

(21) Appl. No.: 09/487,430

(22) Filed: Jan. 19, 2000

(51) Int. Cl.$^7$ .................................................. F24H 1/18
(52) U.S. Cl. ................................. 392/445; 392/471
(58) Field of Search .................... 392/444, 445, 392/447, 449, 450, 451, 471

(56) References Cited

U.S. PATENT DOCUMENTS

| | | | |
|---|---|---|---|
| 3,216,627 | * 11/1965 | Best et al. | 222/249 |
| 3,648,724 | 3/1972 | Lloyd | 137/467 |
| 3,914,804 | 10/1975 | Schrader et al. | 4/7 |
| 3,960,466 | 6/1976 | Taylor | 417/234 |
| 4,092,984 | 6/1978 | Bindel | 128/229 |
| 4,119,113 | * 10/1978 | Meginniss, III | 137/99 |
| 4,178,240 | * 12/1979 | Pinkerton | 210/646 |
| 4,178,931 | 12/1979 | Lind et al. | 128/230 |
| 4,428,507 | 1/1984 | Sneider | 222/105 |
| 5,898,818 | * 4/1999 | Chen | 392/449 |
| 5,946,741 | 9/1999 | Moon | 4/420 |

* cited by examiner

Primary Examiner—Teresa Walberg
Assistant Examiner—Thor Campbell
(74) Attorney, Agent, or Firm—Philip H. Kier

(57) ABSTRACT

A heater for providing steady-temperature heated water for domestic hot water or hygienic purposes. Water is heated in a drum-shaped tank that is divided into two chambers by a piston that can slide longitudinally within the tank. Attached to the tank is a reverse value that can direct cold water from an inlet into either chamber and direct heated water from the other chamber to an outlet leading to a heated water use. Electric component and a cycle regulator control the direction of water flow through the reverse valve and the direction of motion of the piston. When there is a demand for heated water, the cycle regulator causes the piston to move to expel heated water from one chamber while concurrently cold water enters the other chamber. After heated water is expelled from that chamber, the cycle is reversed. Because cold water and heated water are in separate chambers steady-temperature heated water can be maintained. Either electricity or gas can be used in heat water in the tank. When the use of the heated water is for an enema, a flexible connection means, attached to a handgrip and nozzle, is attached to the outlet. When the water heater is used for domestic hot water, the tank is much larger than when used as an enema device.

15 Claims, 10 Drawing Sheets

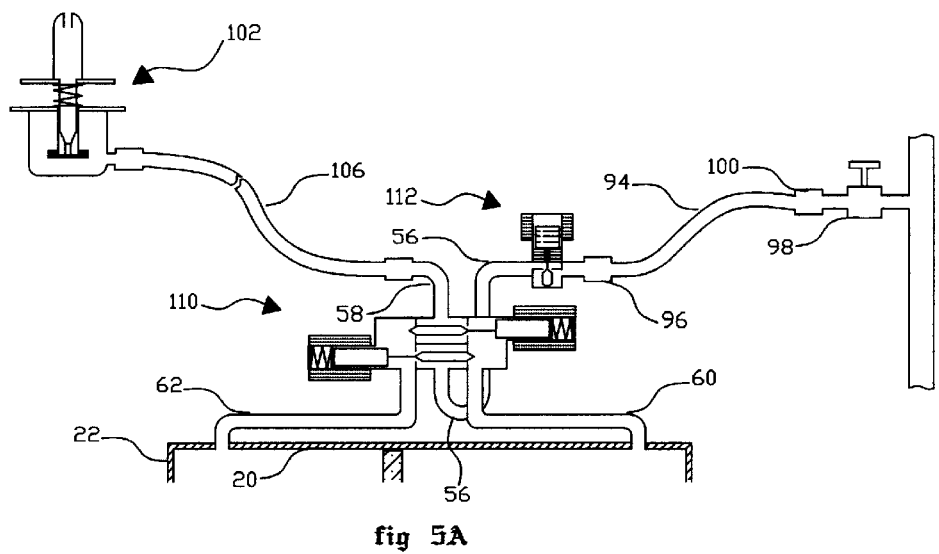
fig 5A
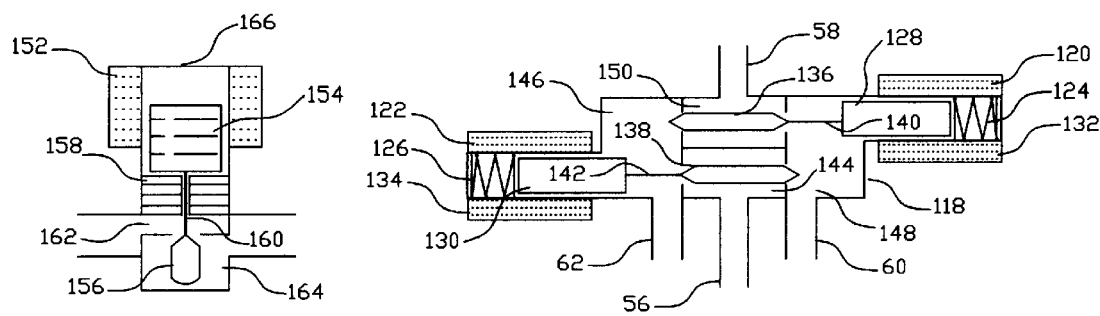
fig. 5B
fig. 5C
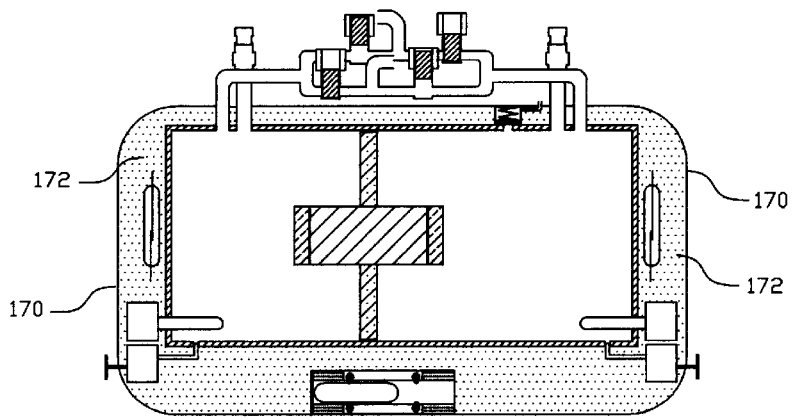
fig. 6

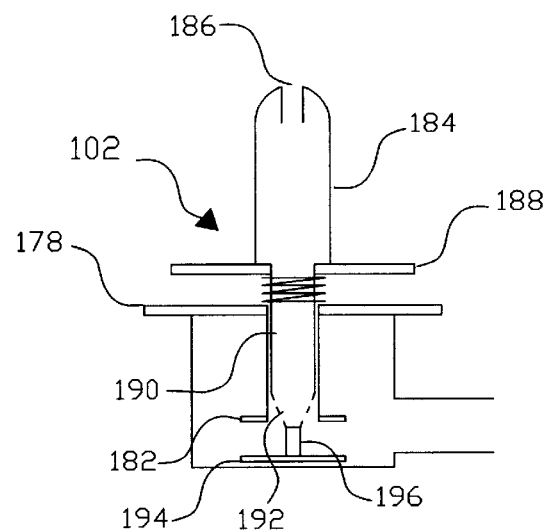
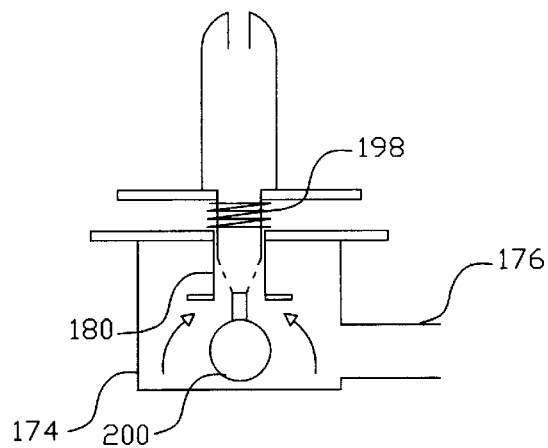
fig. 7A
fig. 7B
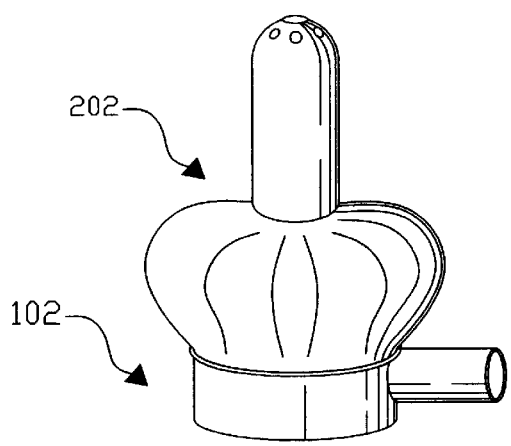
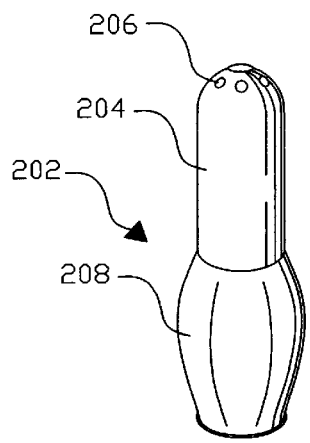
fig. 8B
fig. 8A

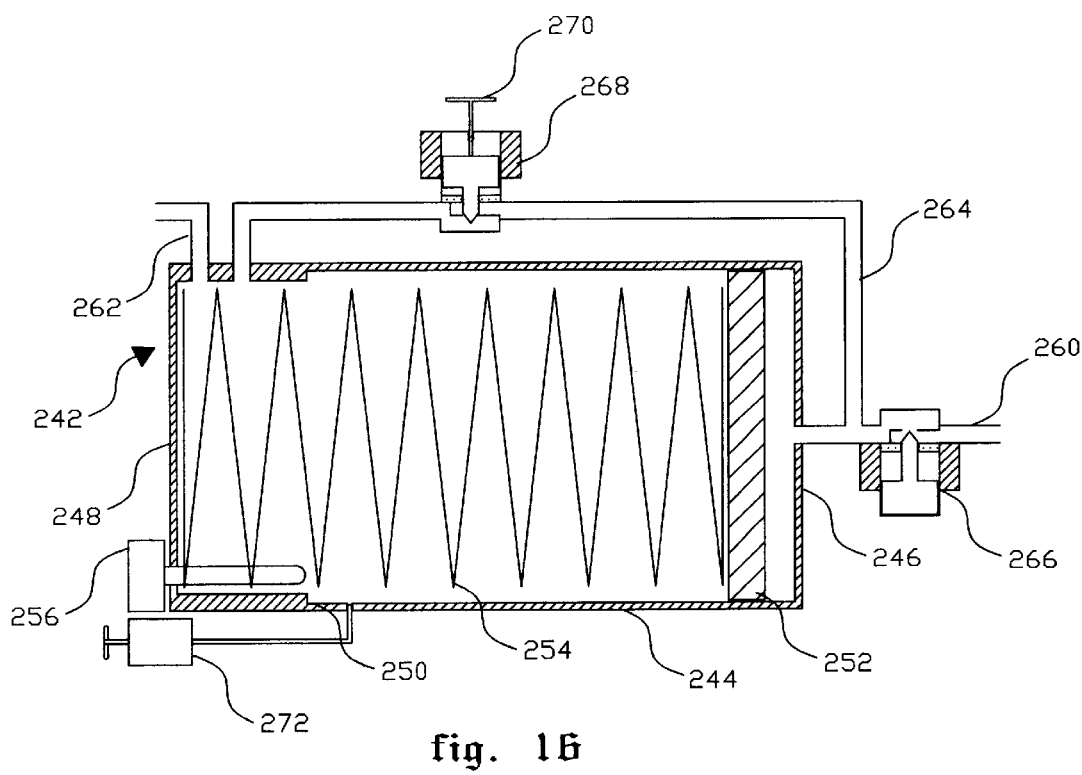
fig. 16
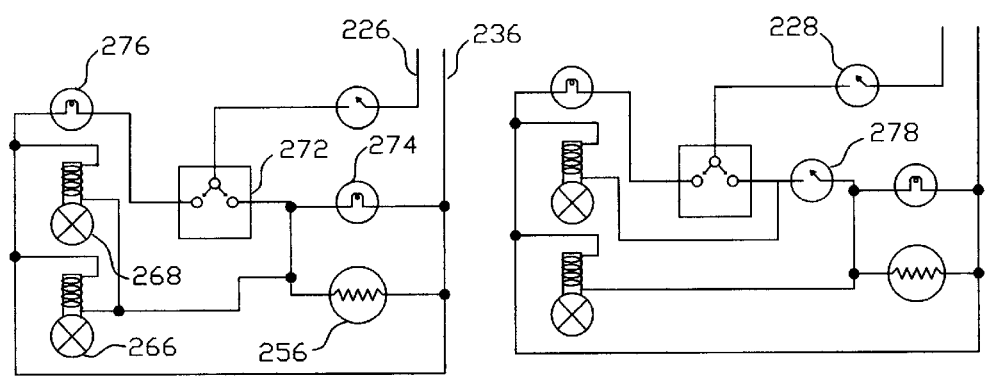
fig. 17                    fig. 18

STEADY-TEMPERATURE WATER HEATER AND ENEMA DEVICE

BACKGROUND

This invention relates to water heaters used for kitchen, bathroom and hygienic purposes. More specifically to water heaters that save energy and water.

Conventional hot water heaters usually heat water up to an average temperature of 80° C. This temperature is too hot for many uses so that it is then mixed with cold water when used in baths and showers, in douches or in enemas. It is wasteful of energy to heat water to too a high temperature and then dilute it as there is a loss of energy during the adjustment in temperature. Another disadvantage of conventional hot water heaters is that water temperature is difficult to control if there are multiple users. If one person is taking a shower and a concurrent user suddenly starts using cold water, the person in the shower could be scalded. Conversely, if the concurrent user suddenly stops using cold water, the person in the shower could be chilled by a sudden slug of cold water. Another disadvantage associated with high temperature water heaters is vulnerability to explosion and fire.

This invention overcomes these disadvantages by providing hot water with a steady temperature regardless of multiple concurrent use or duration of use. The temperature of the water can be set to be in the range of 30–42° C. according to the season and personal preferences so that it need not be mixed with cold water. The temperature of the hot water can be set as high as in a conventional hot water heater if desired.

This invention, because it can provide steady-temperature hot water in the range of 30–42° C., is well suited for hygienic uses, such as douches and enemas, in hospitals and nursing homes as well as in homes. The prior art for enema devices falls into two groups: attachments to toilet plumbing or seat; and freestanding units. Examples of enema devices that are attached to toilets are found in U.S. Pat. No. 5,946,741 to Moon, U.S. Pat. No. 4,092,984 to Bindel, and U.S. Pat. No. 3,648,724 to Lloyd. Examples of freestanding units are found in U.S. Pat. No. 4,178,931 to Lind, U.S. Pat. No. 3.960,466 to Taylor, and U.S. Pat. No. 3,914,804 to Schrader.

Enema devices that are attached to toilets may suffer from several flaws. They may provide water at an inappropriate temperature, usually too cold, for use in douches, enemas, or bidets. They may provide an unknown quantity of water for enema use. Use of too much water could cause serious health problems to some persons, particularly elderly persons with kidney disease, because some water will be absorbed via the large bowel, which could cause water intoxication. Enema devices with a nozzle installed in a toilet seat are vulnerable to contamination with harmful bacteria. Still another disadvantage is the use of long nozzles that could cause rectal or colon injury. Freestanding enema devices suffer from some of the disadvantages of toilet attachment devices and additional disadvantages. Those using a motor and water pump may be expensive. Those using gravity to deliver water may be inconvenient to locate and need preparation before use.

Accordingly, there are several objects and advantages of the present invention. One object is to provide water heater that yields steady-temperature heated water for a variety of uses in an energy-efficient manner. Another object is to provide water heater with enema attachments that is a safe enema device that is always ready for use for bidet sanitation, enema injection, or feminine douche purposes. Another object is to provide a steady-temperature water heater with enema attachments that can deliver a known quantity of warm water. Still another object is to provide a steady temperature water heater with an enema attachment that include an anal plug and short nozzle to prevent injury to the rectum and colon.

SUMMARY OF THE INVENTION

The present invention is a water heater that can deliver warm or hot water at a steady temperature. A large capacity water heater can be used for domestic hot water. A small capacity heater can be used with attachments for hygienic uses, such as enemas. It contains a drum-shaped tank, a piston that can slide longitudinally inside the tank, a gas or electric heater and thermostat at each end of the tank, a reverse valve with four pipes, and electric components including a cycle regulator. The piston divides the tank into two chambers. The reverse valve has one inlet pipe for cold water, one outlet pipe for heated water, and a pipe connected with each chamber. The electric parts and cycle regulator control the direction of water flow through the reverse valve and the direction of motion of the piston. One chamber contains heated water while the other chamber contains cold water from the cold inlet. When there is demand for heated water, the cycle regulator causes the piston to decrease the size of the chamber containing heated water. This causes the heated water to leave that chamber through the reverse valve. Concurrently, cold water is entering the chamber that it is increasing in size and upon entering the chamber is being heated. This chamber will contain heated water for the next cycle in which the direction of motion of the piston is reversed. There is no mixing or contact between heated water and cold water so that heated water with a steady temperature can be provided. In its use in an enema device, a hose is used to connect the outlet pipe with an enema attachment containing a handgrip, or anal plug, and a nozzle. Other embodiments use a different reverse valve and a water heater tank in which inlet water is heated only on one side of the piston.

BRIEF DESCRIPTION OF THE DRAWINGS

FIG. 5A is a cross sectional view of the reverse valve shown in FIG. 4 with a shut-off valve and the enema attachment.

FIG. 5B is a magnified cross sectional view of the shut-off valve in FIG. 5A..

FIG. 5C is a magnified cross sectional view of the reverse valve in FIG. 5A.

FIG. 6 is a cross sectional view of the preferred embodiment of the water heater and reverse valve including insulation and casing.

FIG. 7A is a cross sectional view of a handgrip of the enema attachment with a check valve.

FIG. 7B is a cross sectional view of a handgrip of the enema attachment with a ball valve.

FIG. 8A is a perspective view of a sheath for covering the handgrip of the enema attachment.

FIG. 8B is a handgrip covered by the sheath shown in FIG. 8A.

FIG. 16 is a cross sectional view of an embodiment in which two solenoid valves and a spring replace the reverse valve, one heater, and one thermostat.

FIG. 17 is a circuit diagram for the alternative embodiment shown in FIG. 16 when there is manual control of a solenoid.

FIG. 18 is a circuit diagram for the alternative embodiment shown in FIG. 16 when there is electric control of a solenoid.

DETAILED DESCRIPTION OF THE INVENTION.

Figure 1:
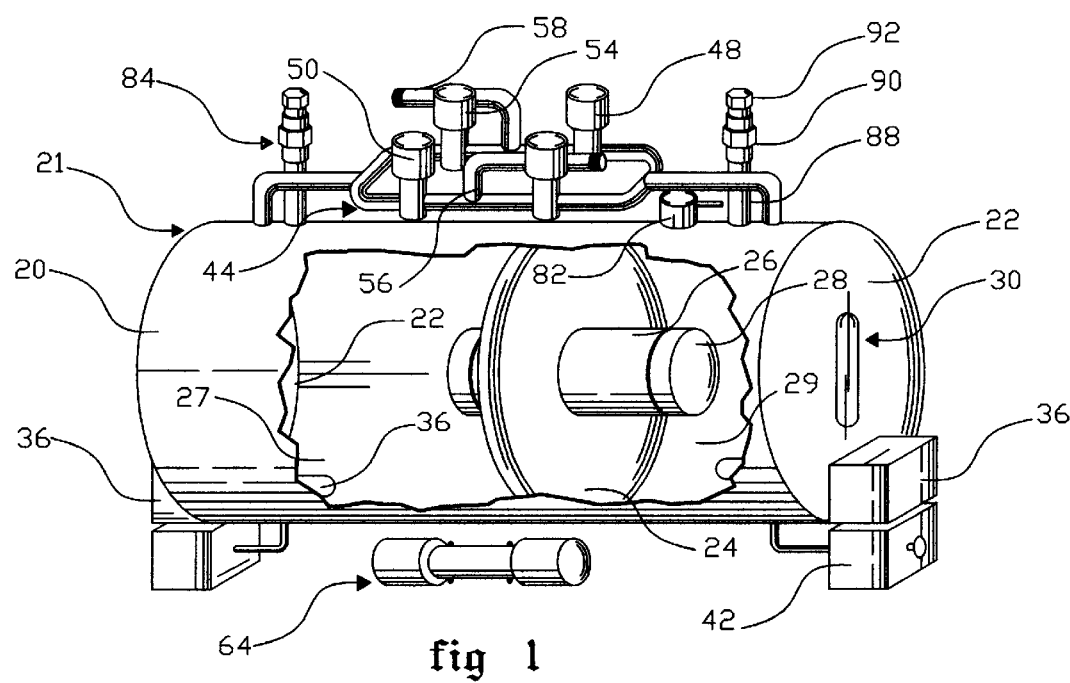
FIG. 1 is a perspective view of the preferred embodiment of the water heater without the casing and insulation, and with part of the tank cut away.
Figure 2:
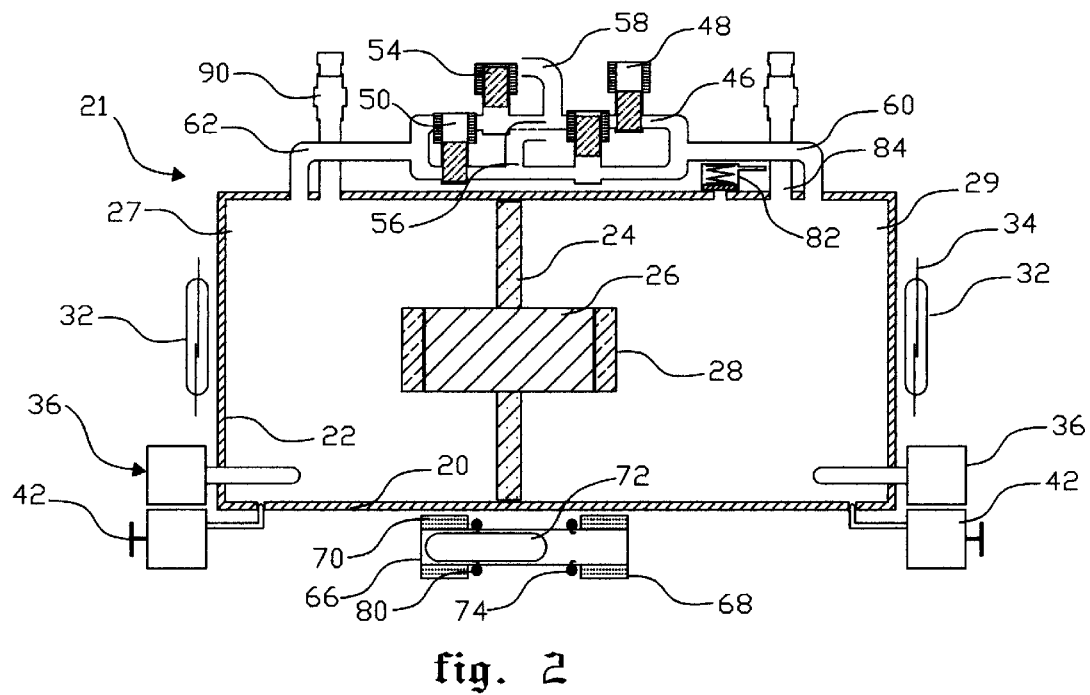
FIG. 2 is a elevation cross sectional view of the same embodiment of the water heater.

With reference to FIG. 1, FIG. 2, and FIG. 6, there is a water heater that includes a cylinder 20, which can be made of glass, aluminum, steel, plastic, or any other material with sufficient strength to withstand the pressure exerted by the water contains within. The cylinder is closed on both ends by discs 22 to form a tank 21. The tank is enclosed in an insulating material 172 and an outer casing 170. The discs can be the same material as the cylinder, except that they cannot be a magnetic material so that they are transparent to a magnetic field. Contained within the cylinder is a thick disc-like piston 24 that has the same diameter as the cylinder's inside diameter The piston divides the interior of the cylinder into a left chamber 27 and a right chamber 29. At the center of the piston is a rod 26 with magnets 28 at each end. The purpose of the rod is to stop the piston from contacting the disc 22. A magnetic switch 30 is attached to the outer side of each disc. A magnetic switch has a case that is transparent to magnetic fields and hosts two magnetic metal leads 34. The leads 34 do not contact each other unless in a magnetic field. Near the bottom of each disc 22 is an electric heater 36 and a thermostat 42. Any kind of thermostat, such as a gas-filled capillary tube, could be used.

Figure 9:
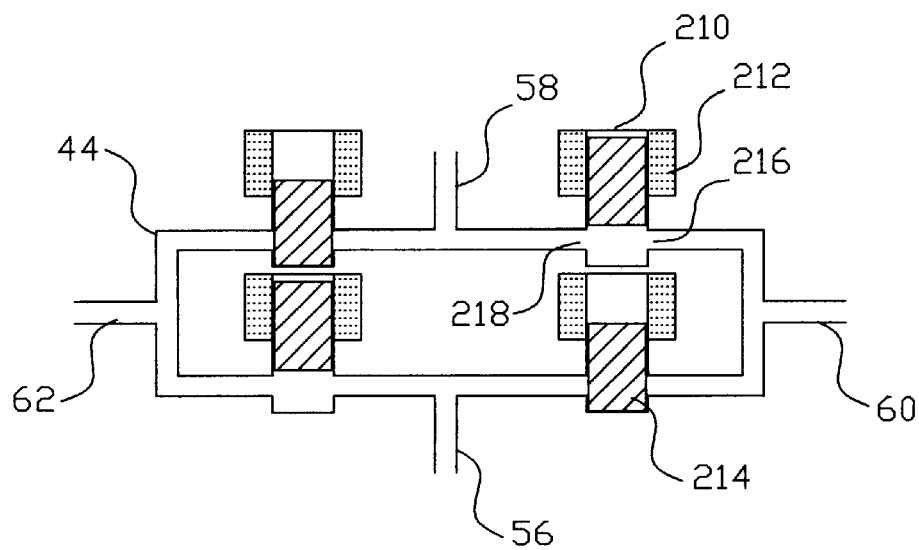
FIG. 9 is a magnified cross sectional view of the reverse valve of the embodiment shown in FIG. 1.

A reverse valve 44 is used to control flow of water into and out of the two chambers in the tank. The reverse valve contains a loop pipe 46, four solenoid valves 48, 50, 52, and 54, an inlet pipe 56 for cold water, an outlet pipe for heated water 58, and two side pipes 60 and 62. Each side pipe connects the reverse valve to a chamber in the water heater tank. Solenoid valves 48 and 50 open and close concurrently and solenoid valves 52 and 54 open and close concurrently. A solenoid valve is closed when no electricity is flowing through its coils; conversely, a solenoid valve is open when electricity is flowing through its coils. As shown in FIG. 9, each solenoid valve consist of a case 210 closed at both sides, an electric coil 212, an iron core 214 that can slide inside case 210, an inlet 216, and an outlet 218. An iron core can plug the inlet 216 and outlet 218 when it slides downward.

This embodiment has a cycle regulator 64 to control the water cycle within the water heater. The cycle regulator has a case 66, two coils 68 and 70, a rod-shaped iron core 72, rounded at both ends which can be slid easily inside case 66 and two or more pairs of contact points 74 and 80. If there are more than two pairs of contact points, the iron core should be subdivided. When electricity passes through coil 70, iron core 72 will be attracted to that coil and make electrical contact between points 80; if coil 68 gets activated, the iron core will be attracted to that coil and make electrical contact between points 74. The position of piston 24 will determine the points between which electrical contact is made. In the event, a thermostat fails to shut off current to its heater, there is a safety valve 82 to relieve pressure and temperature within tank 21. This safety valve may be installed near the middle of the upper surface of the tank. Two air drain pipes 84 are installed near opposite ends of the top of tank 21. Each air drain pipe has a pipe 88 connected to the top of tank 21, a pipe connector 90 and a plug 92. An air drain pipe is open only during installation: during operation, it is closed by its cap 92.

Figure 3:
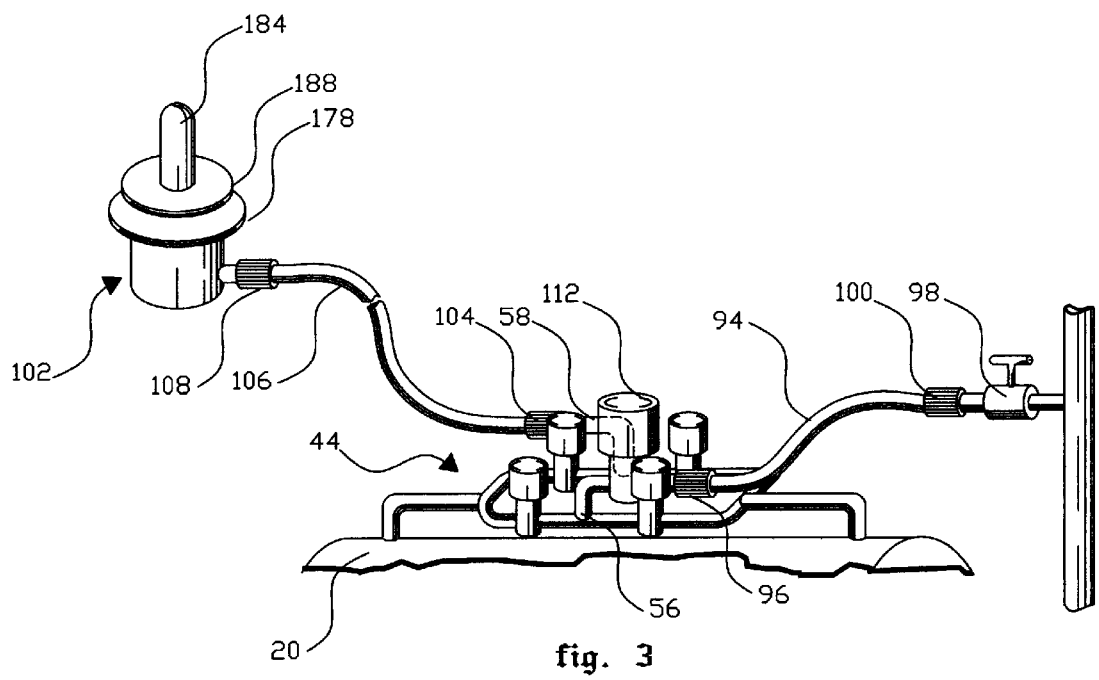
FIG. 3 is a fragmentary view of the reverse valve with a shut-off valve connected to its inlet and enema attachment for the preferred embodiment shown in the preceding figures.

FIG. 3 shows the connections between the reverse valve 44 described above and the cold water supply and between the reverse valve and the enema attachment. The reverse valve connects to the cold water supply 98, which could be a bathroom faucet by means of inlet pipe 56, hose 94, and connectors 96 and 100. The heated water outlet pipe 58 connects to the handgrip 102 of the enema attachment through connector 104, hose 106, and connector 108. A steady-temperature water heater should have a tank 21 with a small capacity when equipped with an enema attachment so that it can be portable (especially for use in a home bathroom) and so that too much water cannot be injected. However, a small capacity tank, whose supply of heated water could be consumed within a few minutes, opens up the possibility that cold water could be injected if more time is needed to heat incoming water. To preclude this possibility, there may also be a shut off valve 112 to prevent flow of cold water through inlet pipe 56.

FIG. 4 and FIGS. 5A through 5C show an alternative embodiment of reverse valve 110. This embodiment has two electric coils 120 and 122, two springs 124 and 126, two iron cores 128 and 130, two cases, 132 and 134. Each case hosts an electric coil, a spring, and an iron core, two plug nails 136 and 138, two connection nails 140 and 142 and four chambers 144, 146, 148, and 150. The inlet leads into chamber 144; the outlet leads from 150; one side pipe 62 leads to chamber 146; the other side pipe 60 leads to chamber 148. There are four perforations between the four chambers: one between chambers 144 and 146; one between chambers 148 and 150; one between chambers 144 and 148; and one between chambers 146 and 150. Activating an electric coil results in a plug nail blocking the perforations between two chambers and opening the perforations between two other chambers. The position of the nail plugs determine which side pipe is accessible to the inlet pipe and which side pipe is accessible to the outlet pipe. There is also a main case 118 hosting the chambers, plug nails, inlet for cold water 56 and outlet for heated water 58.

This embodiment for the reverse valve may also have a solenoid valve 112, which would connect to the inlet pipe 56. The other embodiment of the reverse valve 44 shown in FIG. 3 could also have such a solenoid shut-off valve. Its purpose is to close the inlet pipe 56 in case water that would be leaving a chamber of tank 21 is not sufficiently warm. Solenoid shut-off valve 112 has an electric coil 152, an iron core 154, a plug nail 156, a seat 158 for the iron core, a connection nail 160, two chambers 162 and 164, and a case 166 hosting these parts except for the electric coil 152.

FIGS. 7A and 7B illustrate an embodiment of the enema attachment that consists of a handgrip (anal plug) 102 and a nozzle 184. A user holds the handgrip when inserting the nozzle. The handgrip has inlet pipe 176 which is attached to hose 106, a casing 174, a flange 178 that has a central hole bordered by a tube 180 that ends in a second flange 182. The nozzle 184 has a rounded tip with perforations 186 for ejecting water, a flange 188, and a tube 190 on the opposite side of flange 188 from the rounded tip. Tube 190 is concentric with tube 180 and has a perforated tapered end 192 with a connector 196. There is a spring 198 between flange 178 and flange 188. In the embodiment shown in FIG. 7A, there is a check valve 194 that is in contact with connector 196 when the enema attachment is shut off, that is when water is not entering the nozzle. Instead of a check valve, a ball valve 200 could be used to shut off the flow of water into the nozzle as shown in FIG. 7B. During use, the handgrip and nozzle are first covered by a sheath for sanitary purposes. Then the nozzle 184 is introduce into the anus until the flange 188 contacts anal skin, and by continuing to push flange 188, spring 198 will compress leading to the check valve or ball valve opening so that water can enter the nozzle and be injected from perforation 186 into the anal canal. FIG. 8A shows a sheath 202 with a nozzle cover 204 with perforations 206 and a cover 208 for part of the handgrip that could contact the anal region. FIG. 8B shows the sheath in use.

Figure 10:
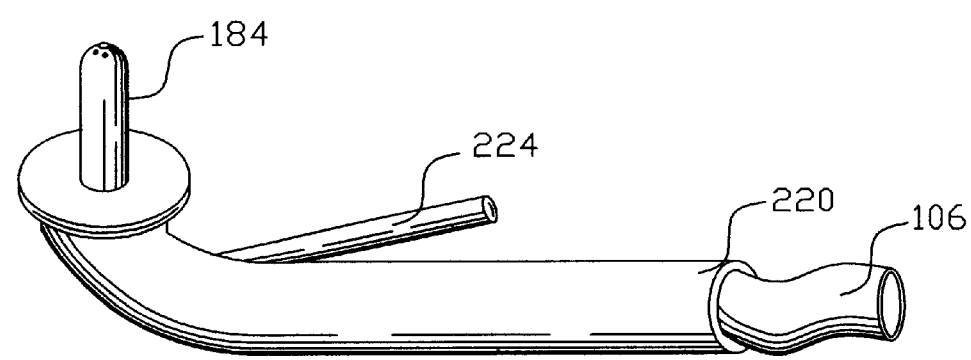
FIG. 10 is a perspective view of an alternative embodiment for a handgrip.

An alternative embodiment of the handgrip is shown in FIG. 10. In this embodiment, the handgrip has a curved handle 220 that connects to hose 106 at one end and to flange 222 at the other end. The nozzle 184 is fastened at the center of flange 222 and a lever 224 is used to open a valve in the handgrip so that water can enter the nozzle.

Figure 11:
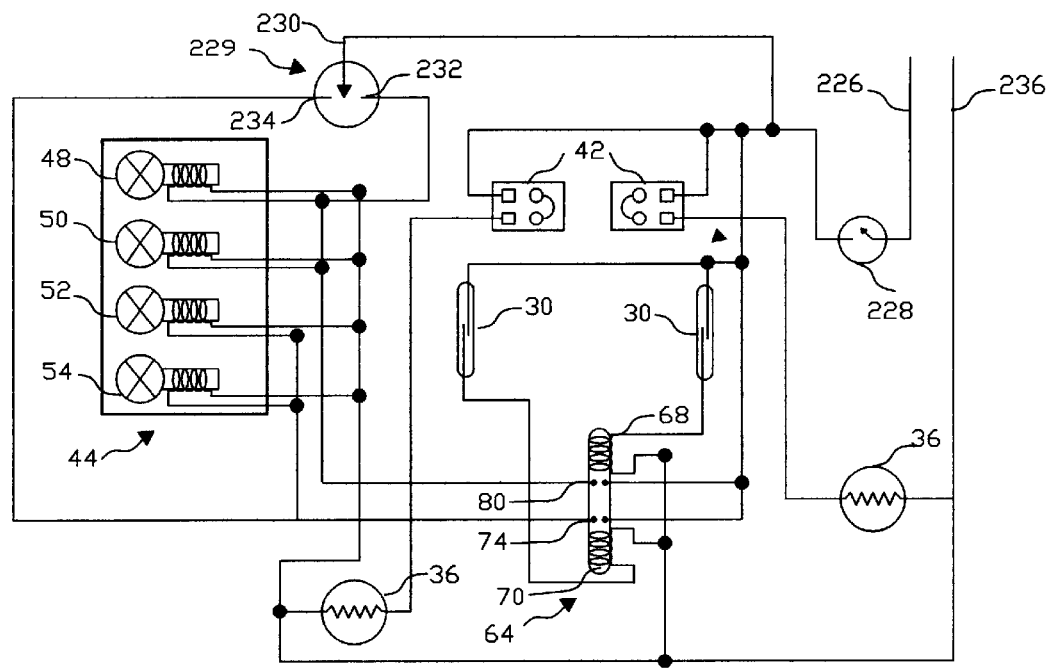
FIG. 11 is a circuit diagram for the embodiment shown in FIG. 1 without a shut-off valve.

FIG. 11 is a diagram of the electric circuit for the embodiment shown in FIG. 1 and FIG. 2. A live line 226 connects to main switch 228 and from it to both thermostats 42, and from each thermostat 42 to its associated heater 36. The live line connects to each magnetic switch 30 directly without passing through the thermostats to contacts points 74 and 80 of the cycle regulator 64 and to center lead 230 of the installation switch 229. One magnetic switch 30 is connected to coil 68 of the cycle regulator and another magnetic switch is connected to coil 70 of the cycle regulator. The installation switch 229 has three leads; the center lead 230 connects directly to the live line, one side lead 232 connects to solenoid valves 48 and 50 and another side lead 234 connects to solenoid valves 52 and 54. Installation switch 228 is used only during installation of the steady-temperature water heater and is keep closed after that. Current passes from contact points 80 of the cycle regulator to coils of the valves 48 and 50 of the reverse valve 44, and from contact points 74 to the coils of the valves 52 and 54. Neutral line 236 connects directly to both electric heaters 36, both coils of the cycle regulator 64, and to all coils of the reverse valve 44.

Figure 12:
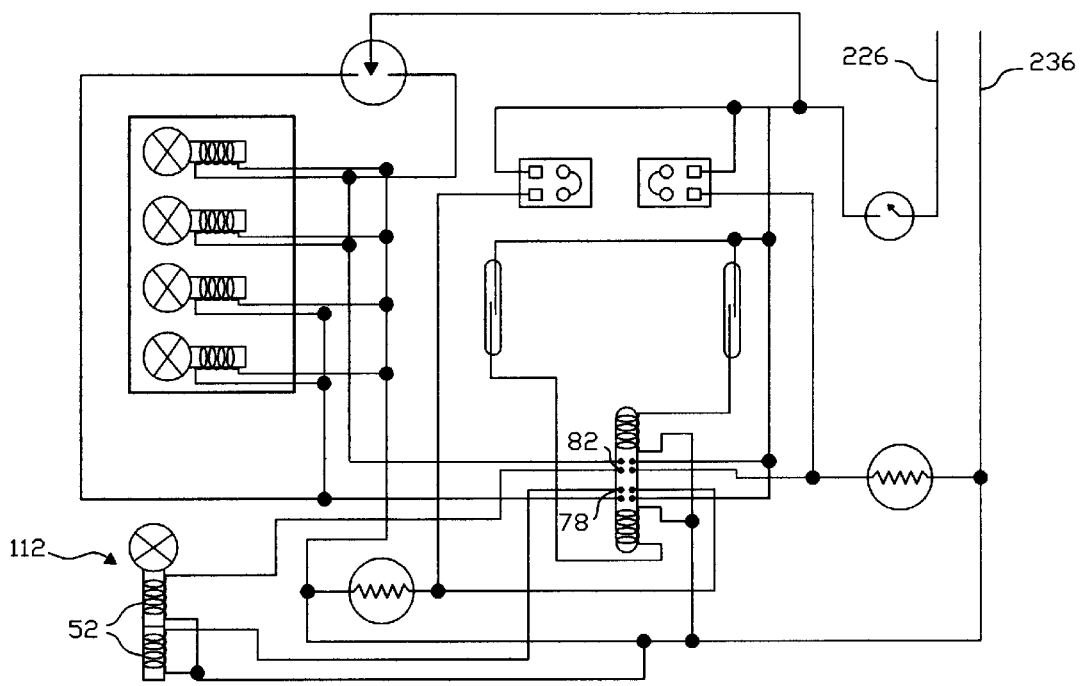
FIG. 12 is a circuit diagram for an circuit for the embodiment shown in FIG. 3, which has a shut-off valve.

FIG. 12 is a diagram of the electric circuit associated with the embodiment illustrated in FIG. 3 that contains solenoid shut-off valve 112, which is intended to shut off the inlet pipe 56 of the reverse valve 44 to stop the flow of the water to the water heater if the water in the outgoing chamber of the tank 21 is not warm enough. This circuit is similar to the circuit shown FIG. 11 except that is shows shut off valve 112, and its coil 52, which has two pairs of two terminals. Each pair of terminals connects parallel to one electric heater 36 through a pairs of contact points 78 and 82 of the cycle regulator 64. This arrangement makes it possible for the heater associated with the outgoing chamber to control shut-off valve 112.

Figure 4:
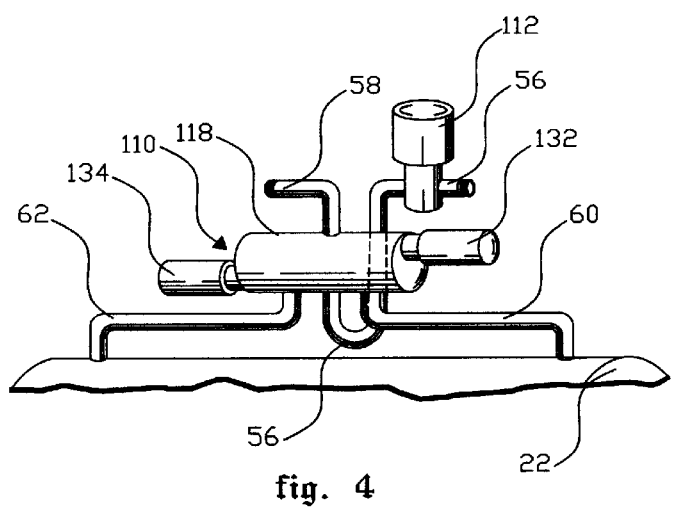
FIG. 4 is a perspective fragmentary view of an alternative embodiment for the reverse valve.
Figure 13:
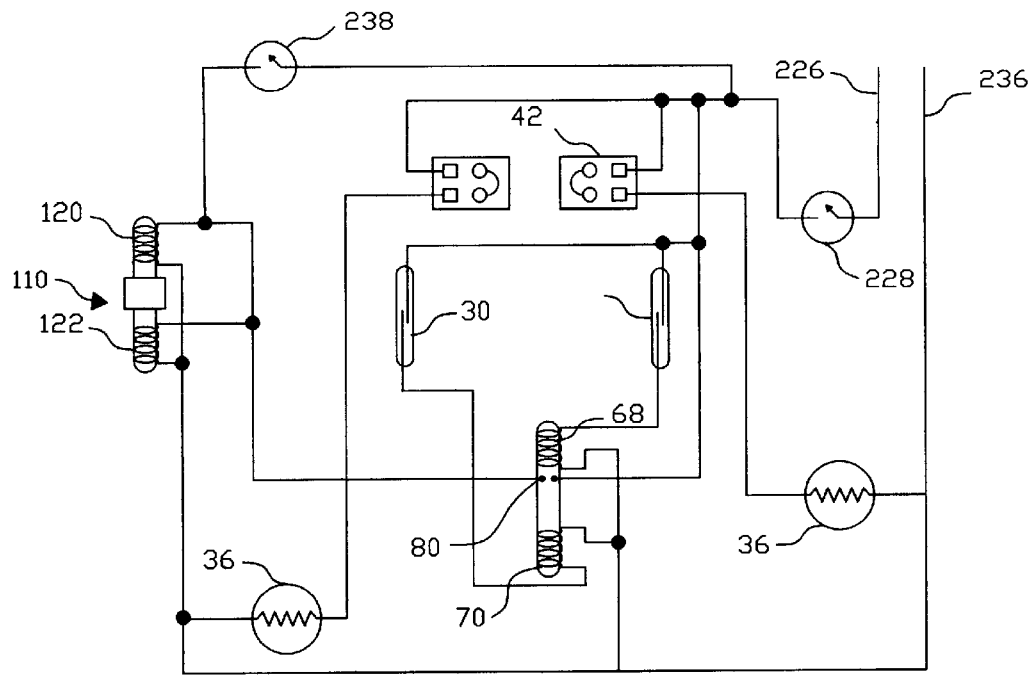
FIG. 13 is a circuit diagram for the embodiment shown in FIG. 4 without a shut-off valve.
Figure 14:
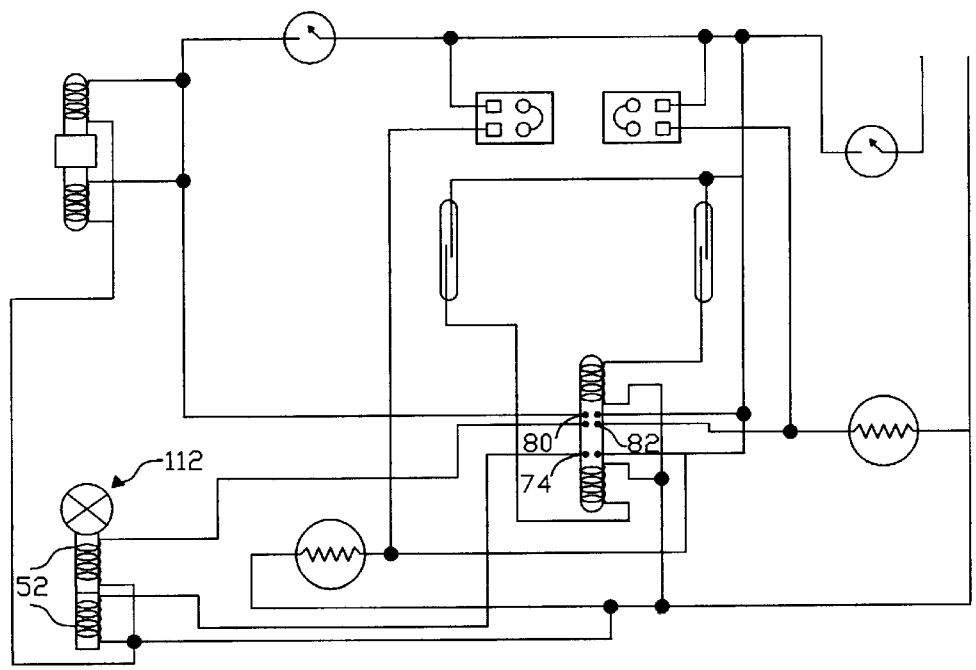
FIG. 14 is a circuit diagram for an alternative electric circuit for the embodiment shown in FIG. 4, which has a shut-off valve.

FIG. 13 is a diagram of the electric circuit of the embodiment shown in FIG. 4 with alternate reverse valve 110 and without shut-off valve 112. The live line 226 connects to main switch 228, and from the main switch to both thermostats 42, to contact point 80 of the cycle regulator 64 and to both magnetic switches 30. Each thermostat is connected to one electric heater 36, and one switch 30 is connected to coil 68 of the cycle regulator while the other another switch 30 is connected to coil 70 of the cycle regulator. Contact point 80 of the cycle regulator is connected to both coils 120 and 122 of the of the reverse valve 110. Installation switch 238, a two way switch (on-off) in use only during installation and keep closed after that, is connect directly to the live line and from it to both coils 120 and 122 of the reverse valve 110. Neutral line 236 connects directly to both heaters 36, to both coils 68 and 70 of the cycle regulator, and to both coils 120 and 122 of the reverse valve 110. FIG. 14 is a diagram of an embodiment with reverse valve 110 and with shut-off valve 112. It shows the additional circuitry associated with shut-off valve 112 and its coils 52.

The water heater components of this invention can be used to supply heated water to an enema attachment or for other uses. The installation of the steady-temperature water heater for the embodiment shown in FIG. 1 is accomplished as follows when the installation is fairly longstanding. Inlet pipe 56 is connected to an incoming cold water supply and outlet pipe 58 is connected to the equipment that uses the heated water. Plug 92 of each air drain pipe 84 is removed from connector 90, installation switch 229 is turned to an On position, both thermostats 42 are turned off, the cold water supply is opened, and the main power switch 228 is turned on. Cold water will flow into one chamber of tank 21, until it is filled (water flowing out of one of the air drain pipes 84 is evidence that the chamber is filled). Then the water supply is shut off and plug 92 is used to close the air drain pipe. Then the process is repeated with installation switch 229 in the other On position to fill the other chamber of the tank. After both chambers are full, the installation switch 229 is closed and sealed, both thermostats are turned on and set, and the cold water supply is opened.

When the water heater and enema attachment are attached to a cold water supply faucet, the installation is as follows. Inlet pipe 56 is connected to the cold water supply, which could be a bathroom faucet, through hose 94 and connectors 96 and 100. Outlet pipe 58 is connected to handgrip 102 through hose 106 and connectors 104 and 108. With reference to FIG. 12, the main power switch 228, is turned on, and the installation switch 229 is turned to an On position.

The handgrip is grasped and flange 188 is pressed against flange 178 until water flows out from nozzle 184. To shut off the water flow, flange 188 is released. These step are repeated with the installation switch turned to the other On position. This process is repeated four to six times and then the installation switch 229 is closed and sealed and both thermostats are turned on.

The embodiment shown in FIG. 4 with circuit diagram shown in FIG. 13, is installed as described above, except that the installation switch 238 is a two-way switch (on-off) instead of a three-way switch (on-off-on). Instead of having a step with the switch in an On position followed by a step with the switch in the other On position, a step with the switch in the on position is followed by a step with the switch in the Off position.

Figure 15A:
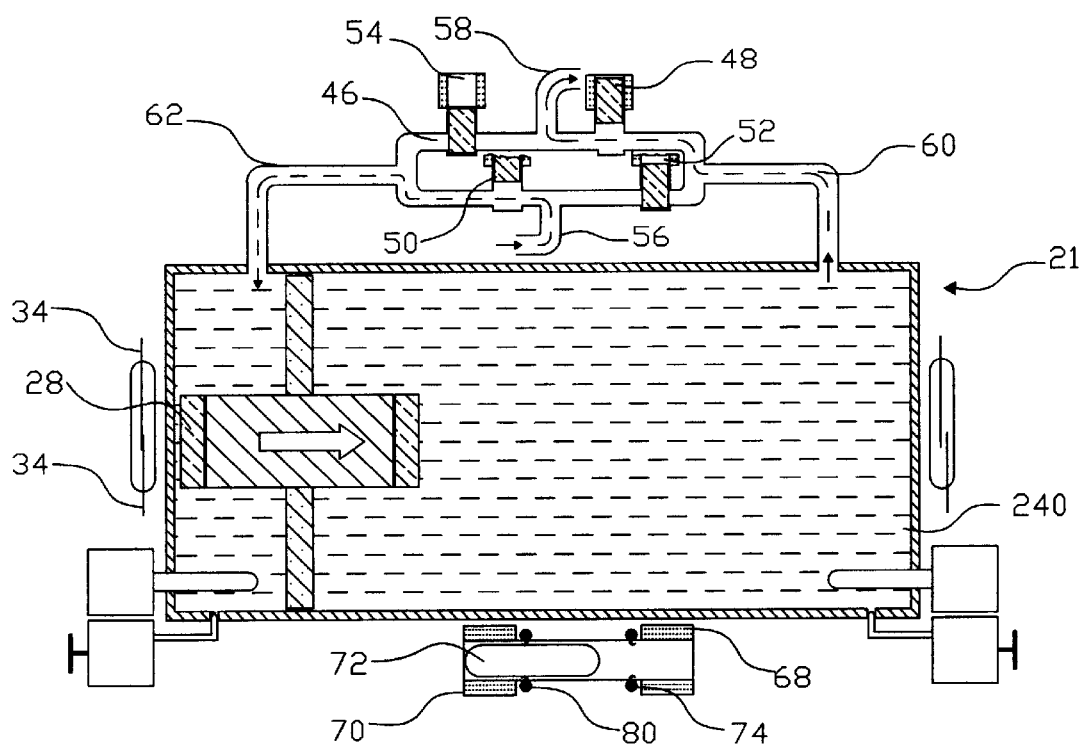
FIG. 15A shows the flow of water inside the water heater tank and reverse valve with the piston moving in one direction.

The operation of the steady-temperature water heater components is explained with reference to FIG. 2, FIGS. 15A, and 15B. This method of operation applies to the embodiments with a shut-off valve 112 (FIG. 3) and with a different design for the reverse valve (FIG. 4). In FIG. 15A, tank 21 and associated pipes are filled with water 240. In FIG. 15A, the piston 24 with magnets 28 are at left side of the tank 21. The left side magnet 28 by induction will magnetize leads 34 of switch 30 and, as a consequence, leads 34 will contact each other to pass electrical current from switch 30 to coil 70 of the cycle regulator 64. Therefore, coil 70 will become magnetized and attract iron core 72 to its side so that iron core 72 makes electric connection between contact points 80. From contact points 80, electric current will pass to solenoid valves 48 and 50 of reverse valve 44 to open them. If the outlet 58 pipe is open, i.e., there is a demand for heated water from the heater, cold water will enter through inlet pipe 56 of the reverse valve 44 to loop pipe 46 through valve 50 to side pipe 62 to left chamber 27 of tank 21. The pressure of the water entering chamber 27 will create a pressure differential on piston 24 forcing it to slide from left to right side. This movement of the piston 24 forces heated water in the right chamber 29 to leave the tank through side pipe 60 and through solenoid valve 48 to outlet pipe 58. The piston will continue sliding from left to right until right side magnet 28 contacts to or get very close to right side disc 22.

Figure 15B:
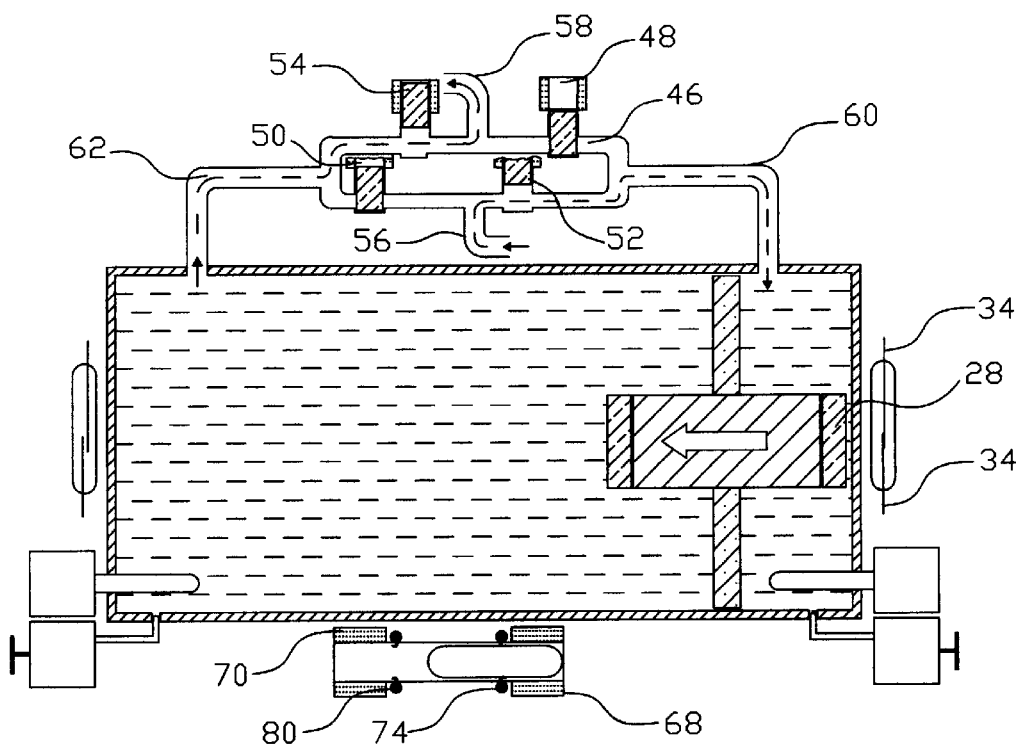
FIG. 15B shows the flow of water inside the water heater tank and reverse valve with the piston moving in the opposite direction.

Now with reference to FIG. 15B, the right side magnet 28 will magnetize leads 34 of the switch 30 by induction, the leads 34 will contact each other and pass electric current to coil 68 of the cycle regulator 64, the coil 68 will attract the iron core 72 to its side so that the iron core makes electrical connection between points 74. From points 74, electric current will pass to valves 52 and 54 of the reverse valve 44 to open them and to close valves 48 and 50. When outlet pipe 58 is open owing to demand for heated water, cold water will flow through inlet pipe 56 to loop pipe 46, through valve 52 to side pipe 60 to right chamber 29. Now pressure of the water entering chamber 29 will force piston 24 to slide from right to left forcing the water in left chamber 27 to move through side pipe 62 to loop pipe 46 through valve 54 to outlet pipe 58. The flow will continue until the left side magnet 28 contacts to or get very close to disc 22; Then the piston will reverse direction and the next cycle will begin. There is no mixing or contact between cold water and warm water inside the tank or connection pipes, so that steady-temperature water is supplied.

An alternative embodiment of the invention that is best suited for use with an enema attachment is shown in FIG. 16. It has a cylinder 244 closed at each end by a disc, 246 and 248, respectively. The cylinder and the discs collectively form tank 242. The wall thickness of the cylinder 244 is greater at the left than along the rest of the cylinder. The junction of the thick walled part of the cylinder 244 and the thin walled part form a stopper edge 250. Within the cylinder is a disc-shaped piston 252 with substantially the same diameter as the internal diameter of the cylinder 244 where it is thin walled. The piston can slide longitudinally within the cylinder without leaking, but its movement to the left is restrained by stopper edge 250. Contained within cylinder 244 between piston 252 and left end disc 248 is a spring 254. Heater 256 has its hot element introduced into the tank 242 to the left of the piston through a sealed perforation or a sealed pocket at the lower part of disc 248. A thermostat 272 and its sensor are introduce into the tank through a sealed perforation or pocket at the interior surface of the wall of cylinder 244 slightly to the right of the stopper edge 250. Tank 242 has an inlet pipe for cold water 260, an outlet pipe for warm water 262, and a bypass pipe 264. The bypass pipe has two terminals; one connects to inlet pipe 260 and the other connects to the tank close to the outlet pipe 262. A reversed solenoid valve 266 connects to inlet pipe 260 and a regular solenoid valve 268 connects to bypass pipe 264. The reversed valve is open during the passive stage (no electric current pass through its coil) and closed during the active stage (when current pass through its coil). Conversely, regular solenoid valve 268 is closed during the passive stage and open during the active stage. Valve 268 has a lever 270 for manual control. If lever 270 is pulled up the valve will open, if released the valve will close. This lever is used during installation only. As before, the tank 242 should contained within insulator and an outer case.

FIG. 17, contains an electric circuit diagram of the alternative embodiment shown in FIG. 16. this electric circuit use when valve 268 is controlled manually during installation. Live line 226 connects to main switch 228 and from it to thermostat 272. Thermostat 272 is a three way thermostat that passes electric current to red light bulb 274, to heater 256, and to both coils of solenoid valves 266 and 268, if it is on. If it is off, the thermostat passes current to green light bulb 276. Neutral line 236 connects to both bulbs 274 and 276, to both coil of the valves 266 and 268, and to the heater 256 directly. FIG. 18, contains the electric circuit diagram of the embodiment of FIG. 16, when valve 268 is controlled electrically during installation. It is similar to circuit of FIG. 17 except that all parts that connect to "on" side of the thermostat 272 except valve 268 pass through installation switch 278.

During installation, inlet pipe 260 connects to a cold water supply through its hose and outlet pipe 262 connects to handgrip through its hose (see FIG. 3 also). Lever 270 of valve 268 is elevated and flange 188 is pressed against flange 178 to open the valve of the handgrip until there is water flow from the nozzle of the handgrip. Then release lever 270 of valve 268, release flange 188 of the handgrip, and then connect the device to electricity to complete installation.

If the embodiment has the electrical circuit of FIG. 18, all the steps described above are followed except that instead of elevating lever 270 of the valve 268, installation switch 278 is turned off and the device is connected to electricity, so that the only valve 268 remains connected to the thermostat. When the valve 268 converts to an open position, cold water will flow into both sides of piston 252 in tank 244 through both inlet pipe 260 and bypass pipe 264 until there is flow from the nozzle of the handgrip. Then turn on the installation switch 278.

After installation, cylinder 244 is filled with cold water with piston 252 and spring 254 in rest position to the right in the cylinder adjacent to disc 246 as shown in FIG. 16.

Because the water is cold, thermostat 272 will turn on and pass current to heater 256, to the coil of reverse valve 266, which will close, and to coil of the regular valve 268, which will open. Consequently, there will be no water flow into or from cylinder 244 while the thermostat at the on position. When the water in the cylinder gets warm, depending the temperature set on the thermostat, it will shut off and cut the electrical current to the heater, to reversed valve 266, which converts to the open position, and to regular valve 268, which converts to the close position. If the user opens the outlet pipe 262 to use the enema attachment, cold water will flow through inlet pipe 260 into tank 242 to the right of piston 252. The pressure of the water entering the tank will cause the piston to slide from right to left forcing warm water to the left of the piston to flow through outlet pipe 262 until the piston is stopped by stopper edge 250 and the sensor of the thermostat 272, which will be to the right of the piston will have contact with cold water. The thermostat will then turn on and current will flow to heater 256, to the coil of the reverse valve 266 to close it, and to coil of the regular valve 268, to open it. The spring 254, which is under compression, will force the piston 252 to slide from left to right so that the spring can resume its rest position. This movement forces the water at the right side of the piston 252 to flow through bypass pipe 264 and through valve 268 to left side of the piston until all cold water is transferred from the right to the left of the piston 252, which will then contact disc 246, and the water to the left of the piston will be heated by the steps described above.

Figure 19:
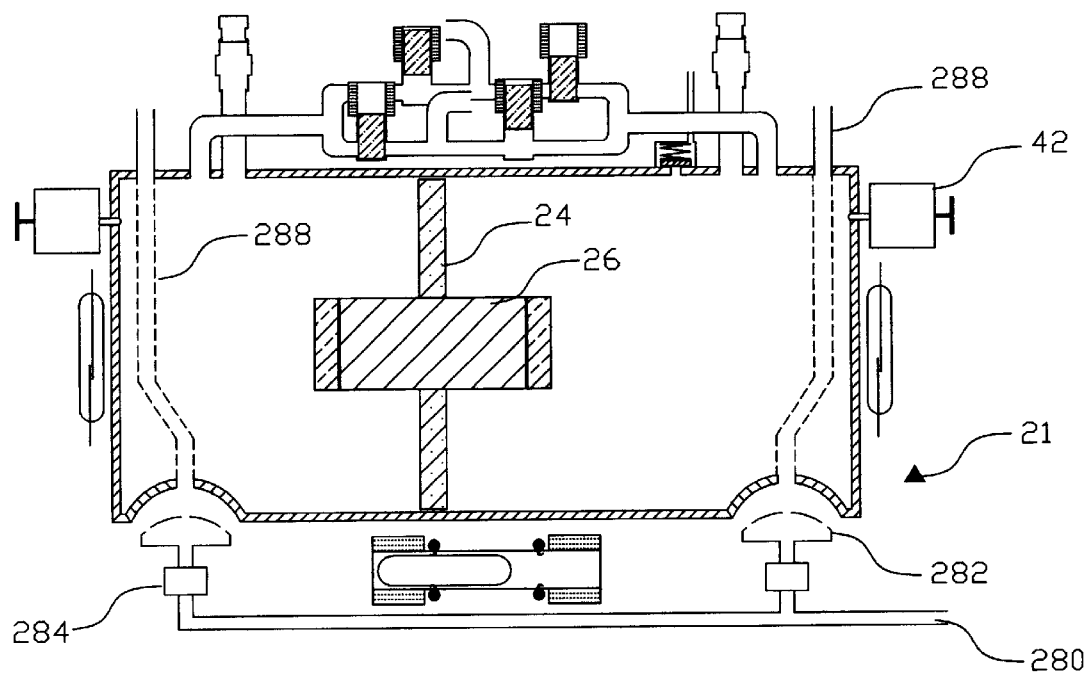
FIG. 19 is an elevation cross sectional view of the steady-temperature water heater when gas-fired heaters are used.
Figure 20:
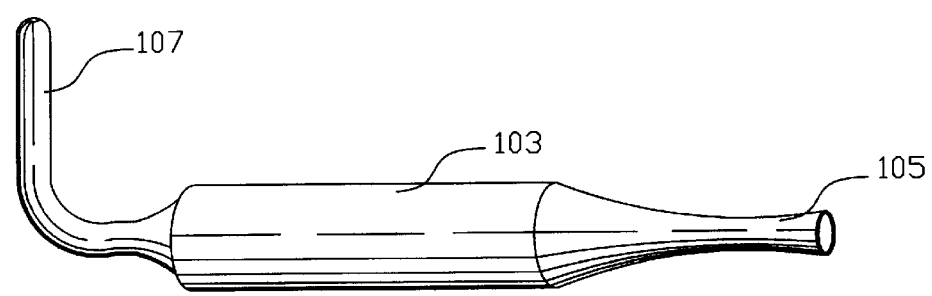
FIG. 20 is a perspective view of an attachment to the nozzle of the enema attachment for dispensing oil or other liquid medications

FIG. 19 shows the configuration for the water heater when natural or bottled gas rather than electricity is used for the heat source. There is a gas burner 282 and a gas-flow control valve 284 adjacent to each chamber of the heater tank 21. These are connected to a gas supply pipe 280. There is also a flame ventilation tube 288 that carries away combustion gases and also transfer heat to the water. This configuration operates in substantially the same way as the configuration with the electric heaters, except that a gas burner substitutes for an electric heat element. This not suitable for the small tanks used with the enema device. The electric circuit for this embodiment differs from that shown in FIG. 11 in that electricity from thermostat 42 flows to the gas-flow control valve 284 instead of electric heater 36.

Sometimes an enema involves injecting an oil or liquid medication into the anal canal. For this purpose a disposable tube 103 with an irrigation tip 107 that is inserted in the anal canal can be attached by means of a connector 105 to the nozzle 184 of an enema attachment. The pressure of water ejected from the nozzle 184 forces oil or liquid medication in the disposable tube 103 to pass through the irrigation tip 107 into the anal canal.

I claim:

1. An electric water heater to produce steady-temperature heated water comprising:
    a cylindrical tank with a right end and a left end, each end made of a non-magnetic material and containing a heater, an electric switch, and a thermostat;
    a longitudinally movable piston contained in the cylindrical tank, the piston dividing the cylindrical tank into a left chamber and a right chamber, and providing a barrier to the movement of water between the left chamber and the right chamber;
    a rod with a right end and with a left end attached to the piston, the right end of the rod and the left end of the rod each containing a magnet;
    a cycle regulator, the cycle regulator receiving signals from an electric switch to reverse the direction of movement of the piston when an electric switch detects approach of a magnet to an end of the tank; and
    a reverse valve with an inlet from a cold water supply, an outlet to a heated water use, a side pipe entering the left chamber, and a side pipe entering the right chamber, the reverse valve allowing water from the chamber toward which the piston is moving to flow through a side pipe and the outlet when a demand for heated water is detected, the reverse valve simultaneously allowing cold water to pass from the inlet and through the other side pipe into the chamber away from which the piston is moving.

2. Apparatus as set forth in claim 1 wherein the heater is an electric heater.

3. Apparatus as set forth in claim 2 wherein the reverse valve has two sets of two solenoid valves, the two sets of solenoid valves operating simultaneously to direct water from the inlet to the side pipe that enters the chamber away from which the piston is moving, and to direct water from the other chamber through the other side pipe to the outlet.

4. Apparatus as set forth in claim 2 further comprising a solenoid valve that closes the inlet when a signal is received from the thermostat in the end of the chamber toward which the piston is moving that water being expelled from that chamber is not sufficiently heated.

5. An electric water heater to produce steady-temperature heated water comprising:
    a cylindrical tank, with a lateral wall whose thickness has a step increase near one end of the cylindrical tank;
    a longitudinal movable piston that divides the cylindrical tank into two chambers;
    a spring, an electric heater element, and a thermostat sensor contained in the lateral wall of the chamber with the step increase in lateral wall thickness, the thermostat sensor being located more than the thickness of the piston from the step increase in wall thickness and causes the thermostat to turn on the electric heater when the water in the chamber with the spring has a temperature below a preset value;
    an inlet leading from a cold water supply to the chamber that does not contain the spring, electric heater element, and thermostat sensor, the inlet containing a reversed valve, the reversed valve closes when in receives a signal from the thermostat that the water in the chamber is cold;
    a bypass pipe connecting the two chambers, the bypass pipe containing a regular valve that opens when it receives a signal from the thermostat that the water in the chamber with the thermostat sensor is cold; and
    an outlet connected to a heated water use and the chamber with the spring, electric heater element, and thermostat sensor.

6. Apparatus as set forth in claim 5 further comprising a nozzle with perforations, a handgrip, and flexible connection means between the handgrip and the outlet.

7. Apparatus as set forth in claim 6 wherein the nozzle contains a flange and the handgrip contains a flange, a valve, and a spring between the flange of the handgrip and the flange of the nozzle, the valve in the handgrip opening to allow water to flow through the nozzle when the flanges are pressed together.

8. Apparatus as set forth in claim 6 wherein the handgrip contains a flange, a valve, and attached to the handgrip is a lever that opens and closes the valve in the handgrip.

9. An electric water heater to produce steady-temperature heated water comprising:

a cylindrical tank with a right end and a left end, each end made of a non-magnetic material and containing an electric heater, an electric, switch, and a thermostat;

a longitudinally movable piston contained in the cylindrical tank, the piston dividing the cylindrical tank into a left chamber and a right chamber, and providing a barrier to the movement of water between the left chamber and the right chamber;

a rod with a right end and a left end attached to the piston, the right end of the rod and the left end of the rod each containing a magnet;

a cycle regulator, the cycle regulator receiving signals from an electric switch to reverse direction of movement of the piston when an electric switch detects approach of a magnet to an end of the tank; and a reverse valve with four chambers, an inlet from a cold water supply enters one chamber, an outlet to a heated water use exits the second chamber, a side pipe enters the third chamber, and another side pipe enters the fourth chamber, there being perforations between the first chamber and the third chamber, the first chamber and the fourth chamber, the second chamber and the third chamber, and the second chamber and the fourth chamber, there also being two valves, each valve opening or closing the flow of water between chambers with perforations by moving a nail to plug a perforation, the reverse valve allowing water from the chamber toward which the piston is moving to flow through a side pipe and the outlet when a demand for heated water is detected, the reverse valve simultaneously allowing cold water to pass from the inlet and through the other side pipe into the chamber away from which the piston moving.

10. An electric water heater to produce steady-temperature heated water comprising:

a cylindrical tank with a right end and a left end, each end made of a non-magnetic material and containing an electric heater, an electric, switch, and a thermostat;

a longitudinally movable piston contained in the cylindrical tank, the piston dividing the cylindrical tank into a left chamber and a right chamber, and providing a barrier to the movement of water between the left chamber and the right chamber;

a rod with a right end and a left end attached to the piston, the right end of the rod and the left end of the rod each containing a magnet;

a cycle regulator, the cycle regulator receiving signals from an electric switch to reverse direction of movement of the piston when an electric switch detects approach of a magnet to an end of the tank;

a reverse valve with an inlet from a cold water, an outlet to a heated water use, a side pipe entering the left chamber, and a side pipe entering the right chamber, the reverse valve allowing water from the chamber toward which the piston is moving to flow through a side pipe and the outlet when a demand for heated water is detected, the reverse valve simultaneously allowing cold water to pass from the inlet and through the other side pipe into the chamber away from which the piston moving;

a solenoid valve that closes the inlet when a signal is received from the thermostat in the end of the chamber toward which the piston is moving that water being expelled is not sufficiently heated; and a nozzle with perforations and a flange, a handgrip containing a flange, a valve, and a spring between the flange of the handgrip and the flange of the nozzle, the valve in the handgrip opening to allow water to flow through the nozzle when the flanges are pressed together.

11. Apparatus as set forth in claim 9 further comprising a solenoid valve that closes the inlet when a signal is received from the thermostat in the end of the chamber toward which the piston is moving that water being expelled from that chamber is not sufficiently heated.

12. Apparatus as set forth in claim 11 further comprising a nozzle with perforations, a handgrip, and flexible connection means between the handgrip and the outlet.

13. Apparatus as set forth in claim 12 wherein the nozzle contains a flange and the handgrip contains a flange, a valve, and a spring between the flange of the handgrip and the flange of the nozzle, the valve in the handgrip opening to allow water to flow through the nozzle when the flanges are pressed together.

14. Apparatus as set forth in claim 12 wherein the handgrip contains a flange, a valve, and attached to the handgrip is a lever that opens and closes the valve in the handgrip.

15. An electric water heater to produce steady-temperature heated water comprising:

a cylindrical tank with a right end and a left end, each end made of a non-magnetic material and containing an electric heater, an electric, switch, and a thermostat;

a longitudinally movable piston contained in the cylindrical tank, the piston dividing the cylindrical tank into a left chamber and a right chamber, and providing a barrier to the movement of water between the left chamber and the right chamber;

a rod with a right end and a left end attached to the piston, the right end of the rod and the left end of the rod each containing a magnet;

a cycle regulator, the cycle regulator receiving signals from an electric switch to reverse direction of movement of the piston when an electric switch detects approach of a magnet to an end of the tank;

a reverse valve with an inlet from a cold water, an outlet to a heated water use, a side pipe entering the left chamber, and a side pipe entering the right chamber, the reverse valve allowing water from the chamber toward which the piston is moving to flow through a side pipe and the outlet when a demand for heated water is detected, the reverse valve simultaneously allowing cold water to pass from the inlet and through the other side pipe into the chamber away from which the piston moving;

a solenoid valve that closes the inlet when a signal is received from the thermostat in the end of the chamber toward which the piston is moving that water being expelled is not sufficiently heated;

a nozzle with perforations, a handgrip, and flexible connection means between the handgrip and the outlet; and an oil injection attachment with a connector to the nozzle, a disposable tube, and an irrigation tip, the connector and the irrigation tip being attached to the disposable tube.

* * * * *